United States Patent [19]
Chiesi et al.

[11] Patent Number: 5,773,029
[45] Date of Patent: Jun. 30, 1998

[54] HIGH SOLUBILITY MULTICOMPONENT INCLUSION COMPLEXES CONSISTING OF AN ACIDIC DRUG, A CYCLODEXTRIN AND A BASE

[75] Inventors: Paolo Chiesi; Paolo Ventura; Maurizio Del Canale; Maurizio Redenti; Daniela Acerbi; Massimo Pasini, all of Parma, Italy; Jösef Szejtli, Budapest, Hungary; Maria Vikmon, Budapest, Hungary; Eva Fenyvesi, Budapest, Hungary

[73] Assignee: Chiesi Farmaceutici S.p.A., Parma, Italy

[21] Appl. No.: 722,220

[22] PCT Filed: Apr. 13, 1995

[86] PCT No.: PCT/EP95/01407

§ 371 Date: Oct. 22, 1996

§ 102(e) Date: Oct. 22, 1996

[87] PCT Pub. No.: WO95/28965

PCT Pub. Date: Nov. 2, 1995

[30] Foreign Application Priority Data

Apr. 22, 1994 [IT] Italy ................................. MI94A0790

[51] Int. Cl.⁶ .............................. A61K 9/10; A61K 47/40
[52] U.S. Cl. ........................................... 424/488; 514/777
[58] Field of Search ................................... 424/484, 488; 514/58, 777; 536/103

[56] References Cited

FOREIGN PATENT DOCUMENTS 8816902  6/1989  France .
9416733  8/1994  WIPO .

*Primary Examiner*—Edward J. Webman
*Attorney, Agent, or Firm*—Oblon, Spivak, McClelland, Maier & Neustadt, P.C.

[57] ABSTRACT

Multicomponent inclusion complexes characterized by the presence of an acidic drug, a base and a cyclodextrin are disclosed. Said complexes have a specific solubility in water.

9 Claims, No Drawings

HIGH SOLUBILITY MULTICOMPONENT INCLUSION COMPLEXES CONSISTING OF AN ACIDIC DRUG, A CYCLODEXTRIN AND A BASE

The invention relates to multicomponent inclusion complexes basically consisting of a drug bearing an acidic group (hereinafter defined as acidic drug), a cyclodextrin and a base.

In Italian Patent application no MI93 A 000141, three-component inclusion complexes consisting of a basic-type drug, a cyclodextrin and an acid, characterized by a very high solubility in water, were described.

The drugs used in the formation of these complexes, in the presence of the organic or inorganic acid which acts as a counter-ion, give rise to amphyphilic structures, i.e. characterized by a strongly hydrophobic group and an hydrophilic polar head.

It is known that the molecules with such a structure have colloidal properties in aqueous solutions, i.e. they are capable of forming aggregates at suitable concentration and of lowering the surface tension of the solvent: in other words, they act as surfactants.

Among the classes of compounds which have mostly been studied from this aspect (Attwood D., Florence A. T., Surfactant Systems, their chemistry, pharmacy and biology, Chapmam and Hall, UK, 1983) are the diphenylmethane derivatives and the tricyclic derivatives, some of which (terfenadine, tamoxifen, cyclobenzaprine) turned out to be excellent agents for the formation of the multicomponent complexes.

Therefore, it has been assumed that the high, unexpected increase in the solubility of the hydrophobic guest drug and of the cyclodextrin which is observed when the multicomponent complexes are dissolved in water, is due to a reciprocal, synergistic effect of a component on the other: in other words, the cyclodextrin would increase the guest solubility by complexation, whereas the guest, once reached a concentration in solution sufficient to give aggregates and/or micells would act as a surfactant towards the cyclodextrin.

The preparation processes, which consist in removing solvent from a supersaturated solution of the components, would favour such a mutual interaction.

Measurements of the relaxation time "spin-lattice" on the proton and "spin-spin" on the carbon carried out on the multicomponent complex terfenadine-tartaric acid-β-cyclodextrin confirmed that the drug guest is certainly aggregated in solution and therefore it is capable of acting as a surfactant.

Now it has surprisingly been observed that the aggregation also remains in the presence of cyclodextrins, contrary to what reported in literature.

It is known, in fact, that cyclodextrins generally increase the critical micellar concentration (c.m.c.) this creating conditions unfavourable to micellation [Casu B., Grenni A., Naggi A. and Torri G., In Proceedings of the Fourth International Symposium on Cyclodextrin, Eds. O. Huber and J. Szejtli., Kluwer Academic Publishers, Dordrecht, 1988, pp. 189–195; Satake I., Ikenoue T., Takeshita T., Hayakawa K. and Maeda T., Bull. Chem. Soc. Jpn., 58, 2746–2750 (1985) ].

A number of examples of formation of complexes with cyclodextrins in the presence of conventional surfactants are reported in literature [R. Palepu, J. E. Richardson, V. C. Reinsborough: Langmuir 1989, 5, 218–221; G. Nelson, I. M. Warner: Carbohydr. Res. 1989, 192, 305–312] and the formation of complexes of cyclodextrins with amphyphilic drugs was described by Takiwasa N. et al. in Colloid. Polym. Sci. 1993, 271(5) which characterized the thermodynamic properties thereof.

Up to now, however, no examples are known using the intrinsic surfactant properties of the included molecule to obtain very soluble complexes as far as both the included molecule and the cyclodextrin itself are concerned.

This principle was verified by the Applicant also for acidic drugs having a potentially amphyphilic structure.

Thus it has been found, and it is the object of the present invention, that also with acidic molecules, the simultaneous salt formation with suitable basic counter-ions and complexation with cyclodextrins, dramatically increases the aqueous solubility.

Usually, as for basic drugs addition salts with organic or inorganic acids are prepared to enhance solubility, analogously for acidic drugs salts with organic or inorganic bases are used.

The preparation of these salts, in order to increase solubility, in many cases only favours the preparation of the pharmaceutical formulation, without involving a real advantage in terms of an enhanced absorption.

In fact, it often happens that the dissociation constant of the salt is higher than the pH of the medium in which the absorption takes place (mucosa, cutis or plasma) whereby even administering the salt in the absorption site the drug is found in the form of the free acid.

In the case of acidic drugs also the poor solubility and the subsequent reduced bioavailability can be improved by means of the complexation with cyclodextrins.

In the prior art a lot of examples of acidic drugs complexed with cyclodextrins with good results are described.

Now it has surprisingly been found that the formation of complexes of acidic drugs with cyclodextrins (CD) in the presence of bases in set molar ratios gives rise to the formation of complexes easily soluble in water with very high concentrations of both guest and host molecules.

The general method for the preparation of acidic drug:CD:base complexes is based on the usual principle of removing solvent from a supersaturated solution of the components, and it involves the following steps:

a) suspension: suitable amounts of drug, cyclodextrin and base in defined stoichiometric amounts are suspended in distilled water or other suitable solvent;

b) homogenization: the suspension is homogenized by stirring and/or sonication until obtaining an opalescent solution;

c) filtration: the solution is filtered, with a suitable system, until obtaining a clear solution;

d) drying: water or solvent is removed by conventional techniques such as freeze-drying, spray-drying, drying in oven and the like.

With the same method, complexes with alfa or gamma CD, hydroxypropyl-βCD (HPBCD), dimethyl-βCD (DIMEB), RAMEB (Random Methylated β-cyclodextrin) or other cyclodextrin derivatives can be prepared to obtain, with the most soluble βCD derivatives, even more concentrated solutions with good stability characteristics which can give liquid pharmaceutical preparations for oral or parenteral use.

The basic component of the complexes according to the invention can be of both inorganic and organic nature.

Specific examples of bases comprise alkali or alkaline-earth hydroxides, secondary or tertiary amines, such as diethanolamine, triethanolamine, diethylamine, methylamine, tromethamine (TRIS) and the like.

By acidic drug any drug is meant having at least an acidic function such as a carboxy, sulfonic, sulfonylamino, sulfonylureic, phenol group and the like.

Examples of classes of acidic drugs comprise oxicams, hypoglycemic sulfonylureas, benzothiadiazine diuretics, barbturic acids, arylacetic and arylpropionic antiinflammatory acids.

The molar ratios of the cyclodextrin or derivative can vary from 0.5 to 10 per mole of drug, whereas the molar ratios of the basic component can vary from 0.1 to 10 moles, per mole of drug.

The invention is illustrated in detail by the following examples.

The examples relates to drugs belonging to different chemical and therapeutical classes, selected as particularly significant test molecules, based on their characteristics, to exemplify the invention.

However, the invention itself can obviously be applied to any other suitable acidic molecule.

EXAMPLE 1
Preparation of glibenclamide-βCD-sodium hydroxide soluble complexes 20 mmoles of sodium hydroxide are dissolved in 1 liter of distilled water. This solution is added with, in sequence, 60 mmoles of βCD and 20 mmoles of glibenclamide. with stirring. The suspensions are homogenized by strong stirring and sonicated until obtaining slightly opalescent solutions. The solutions are filtered through a sintered glass pre-filter. The solid complexes are obtained by freeze-drying the clear solution. The X ray diffraction pattern of the product shows a completely amorphous structure.

EXAMPLE 2
Preparation of glibenclamide-βCD-diethanolamine complexes 1 mmole of glibenclamide and 2 mmoles of βCD are suspended in 60 ml of distilled water. Then the suspension is added with 1 to 4 mmoles of diethanolamine and sonicated for some minutes. The resulting clear or slightly opalescent solutions are filtered through a sintered glass pre-filter. The resulting solutions are freeze-dried.

EXAMPLE 3
Preparation of other glibenclamide-βCD-organic bases complexes

With a process analogous to the one of the above examples, the following complexes were prepared:
3a) glibenclamide (1 mmole) -βCD (1 mmole)—triethanolamine (2 mmoles) in a 1:1:2 ratio;
3b) glibenclamide (1 mmole) -βCD (1 mmole)—diethylamine (2 mmoles) in a 1:1:2 ratio;
3c) glibenclamide (1 mmole) -βCD (1 mmole)—triethylamine (2 mmoles) in a 1:1:2 ratio;
3d-e-f) glibenclamide-βCD-triethanolamine (or diethylamine or triethylamine) in a 1:2:2 ratio;
3g) glibenclamide (1 mmole) -βCD (1 mmole)—TRIS (7 mmoles) in a 1:1:7 ratio;
3h) glibenclamide (1 mmole) -βCD (2 mmoles)—TRIS (7 mmoles) in a 1:2:7 ratio.

EXAMPLE 4
Preparation of piroxicam-DIMEB-sodium hydroxide complexes 50 mmoles of piroxicam and 100 mmoles of DIMEB are suspended in 420 ml of distilled water. 50 ml of a 1N sodium hydroxide solution are added with continuous stirring. The resulting solution is filtered and the complex is separated by freeze-drying.

EXAMPLE 5
Preparation of piroxicam-γCD-inorganic bases complexes 6 mmoles of piroxicam and 12 mmoles of CD are suspended in 100 ml of distilled water. 8 ml of a 1N sodium hydroxide (or potassium or ammonium) solution are added with stirring. The solution is neutralized until a fine precipitate of the complex is obtained (pH 8–10).

The complex is separated by filtration and dehydrated in oven at 40°–50° C. With a similar process, the complex piroxicam-βCD-sodium hydroxide in a 1:1:1 ratio was prepared.

EXAMPLE 6
Preparation of piroxicam-HPβCD-NaOH complexes 10 mmoles of piroxicam and 10 or 20 mmoles of HPβCD (substitution degree 4.2) are suspended in 100 ml of distilled water. 10 ml of a 1N NaOH solution are added with stirring. The resulting solution is filtered and the complexes are separated by freeze-drying.

EXAMPLE 7
Preparation of other complexes of piroxicam with cyclodextrins and organic bases. With a process analogous to the one of example 6, the following complexes were prepared:
piroxicam-βCD-diethanolamine in a 1:2:1 and 1:2:2 ratio;
piroxicam-γCD-diethanolamine in a 1:2:1 and 1:2:2 ratio.

EXAMPLE 8
Preparation of chlorotiazide-cyclodextrin-organic base complexes

With a process analogous to the one of the above examples, the following complexes were prepared:
chlorothiazide-γCD-lysine in a 1:1:2 and 1:2:2 ratio;
chlorothiazide-HPβCD-lysine in a 1:1:2 and 1:2:2 ratio;
chlorothiazide-βCD-lysine in a 1:1:2 and 1:2:1 ratio;
chlorothiazide-βCD-diethanolamine in a 1:1:2 ratio;
chlorothiazide-HPβCD-diethanolamine in a 1:1:1, 1:1:2, 1:2:1 and 1:2:2 ratio;
chlorothiazide-γCD-diethanolamine in a 1:1:2 and 1:2:2 ratio;
chlorothiazide-HPβCD-ethanolamine in a 1:2:1 and 1:2:2 ratio;
chlorothiazide-HPβCD-triethanolamine in a 1:1:2, 1:2:1 and 1:2:2.

The most significant solubility data of some complexes of the invention are reported in Tables 1–5, in which they are compared with those of the starting compounds and of other systems.

EXAMPLE 9
Preparation of ibuprofen/βCD/triethanolamine 1:1:1 complex

With a process analogous to the one of the above examples, a complex with 0.21 g (1.0 mM) of ibuprofen, 1.1 g (1.0 mM) of βCD and 0.15 g (1.0 mM) of triethanolamine was prepared.

The water solubility of ibuprofen was 9 mg/ml.

EXAMPLE 10
Preparation of indometacin/βCD/triethanolamine 1:2:2 complex

With a process analogous to the one of the above examples, a complex with 0.24 g (0.64 mM) of indometacin, 1.53 g (1.17 mM) of βCD and 0.20 g (0.64 mM) of triethanolamine was prepared.

The water solubility of indometacin was 7.2 mg/ml.

EXAMPLE 11

Preparation of furosemide/βCD/diethanolamine 1:2:2 complex

With a process analogous to the one of the above examples, a complex with 0.22 g (0.64 mM) of furosemide, 1.53 g (1.17 mM) of βCD and 0.13 g (0.64 mM) of diethanolamine was prepared.

The water solubility of furosemide was 7.8 mg/ml.

TABLE 1

Equilibrium solubility, at room temperature, at different pH values, of Glibenclamide (G), its sodium salt (G—Na), and a physical mixture thereof with βCD (G/βCD) in a 1:1, 1:2, 1:3.

| | Solubility [mg/ml] | | | | |
| | | | G/βCD | | |
| pH | G | G—Na | 1:1 | 1:2 | 1:3 |
| --- | --- | --- | --- | --- | --- |
| 4.0 | 0.004 | | | | |
| 7.39 | 0.0188 | | | | |
| 7.5 | 0.020 | | | | |
| 8.35 | | | | | 5.04 |
| 8.47 | | | | 4.64 | |
| 8.53 | | | 3.49 | | |
| 8.89 | 0.299 | | | | |
| 9.0 | 0.600 | | | | |
| >9.3 | | 7.0 | | | |
| 9.53 | 0.768 | | | | | pKa of Glibenclamide: 6.8.

TABLE 2

Instant solubility, at room temperature, at various times, at different pH values, of multicomponent Glibenclamide/βCD/Diethanolamine (G/βCD/DEtOH) and Glibenclamide/βCD/NaOH (G/βCD/NaOH) complexes.

| | | Solubility [mg/ml] | | | | |
| | time | G/βCD/DEtOH | | G/βCD/NaOH | | |
| pH | [min] | 1:2:3 | 1:2:4 | 1:1:1 | 1:2:1 | 1:3:1 |
| --- | --- | --- | --- | --- | --- | --- |
| 1.4 | 15 | 0.10 | 0.10 | | | |
| | 20–30 | | | 0.10 | 0.10 | |
| | 40 | | | | | 0.110 |
| 5.38 | 10 | | | | 0.17 | |
| 5.61 | 10 | 0.24 | | | | 0.24 |
| 6.50 | 10 | 1.16 | | | | 1.16 |
| 7.03 | 10 | | | | 0.82 | |
| 7.3 | 15 | 21.5 | | | | |
| 7.8 | 60 | | | | 42.5 | |
| 9.1 | 05 | | | 33 | | |
| 9.29 | 60 | | 9.6 | | | |

TABLE 3

Glibenclamide concentrations versus time obtained by dissolution at room temperature in pH = 5 and pH = 1,4 buffer of Glibenclamide (G), a physical mixture thereof with βCD (G/βCD) and multi-component Glibenclamide/βCD/NaOH (G/βCD/NaOH) complexes.

| | | Solubility [mg/ml] | | | |
| pH | time [min] | G/βCD/NaOH 1:2:1 | G/βCD/NaOH 1:3:1 | G/βCD 1:2 | G |
| --- | --- | --- | --- | --- | --- |
| 5.0 | 05 | 0.61 | | <0.01 | <0.01 |
| | 10 | 0.81 | | <0.01 | <0.01 |
| | 20 | 0.36 | | <0.01 | <0.01 |
| | 40 | 0.23 | | <0.01 | <0.01 |
| | 50 | 0.27 | | <0.01 | <0.01 |
| 1.4 | 05 | | 0.110 | | <0.01 |
| | 15 | | 0.114 | | <0.01 |
| | 30 | | 0.110 | | <0.01 |
| | 40 | | 0.110 | | <0.01 |
| | 50 | | 0.080 | | <0.01 |

TABLE 4

Equilibrium solubility (eq.) and instant solubility at various times, at room temperature, at different pH values, respectively of Piroxicam (P) and multicomponent Piroxicam/RAMEB/NaOH (P/RAMEB/NaOH) and Piroxicam/HPβCD/NaOH (P/HPβCD/NaOH) complexes.

| | | Solubility [mg/ml] | | |
| | time | | P/RAMEB/NaOH | P/HPBCD/NaOH |
| pH | [min] | P | 1:2:1 | 1:1:1 | 1:2:1 |
| --- | --- | --- | --- | --- | --- |
| 1.2 | eq. | 0.108 | | | |
| 6.0 | eq. | 0.076 | | | |
| 6.25 | 10 | | | 12 | |
| 7.0 | eq. | 0.570 | | | |
| 7.5 | eq. | 1.030 | | | |
| 8.6 | 15 | | | | 45 |
| 8.9 | 15 | | | 75 | | note: Piroxicam pKa is 6.3; the solubility of multicomponent complexes was evaluated both at a pH lower than pKa and at pH values higher than pKa.

TABLE 5

Chlorothiazide concentrations obtained by dissolution at room temperature in water of a Chlorothiazide/HPBCD physical mixture, Chlorothiazide/cosolubilizer and multicomponent Chlorothiazide/HPβCD/cosolubilizer systems.

| System | molar ratio | Solubility [mg/ml] |
| --- | --- | --- |
| C/HPβCD/lysine multicomponent | 1:2:1 | 60 |
| C/lysine physical mixture | 1:1 | 1.25 |
| C/HPβCD physical mixture | 1:2 | 0.34 |
| C/HPβCD/triethanolamine multicomponent | 1:2:2 | 125 |
| C/triethanolamine physical mixture | 1:2 | 2.9 |
| C/HPβCD physical mixture | 1:2 | 0.34 | note: Chlorothiazide has an equilibrium solubility, at room temperature, varying as a function of pH, from 0.4 to 0.7 mg/ml about, and at pKa of 6.7 and 9.5.

In Table 1 and 4 the equilibrium solubility of some drugs used for the preparation of the complexes of the invention was determined, since for the compounds as such the respective sodium salts and the physical mixture with βCD the maximum solubility conditions are obtained at equilibrium.

On the contrary, in the case of the complex, (as in Tables 2 and 4), the instant solubility is determined, since in most cases to define the maximum solubility of a complex, also the supersaturation solubility appearing in a set time interval (which varies depending on the complex and is indicated in the Table every time) immediately after the dissolution.

The Tables also evidence that the complexes of the invention attain a remarkable increase in solubility, compared with the starting compounds.

This increase in solubility cannot be ascribed only to the complexation of the drug, since it also occurs at pH values at which no ionization of the cyclodextrin hydroxyls is observed.

The water solubilities of acidic drugs and of β-cyclodextrin in some complexes of the invention are represented in Table 6.

TABLE 6

| Complex | | guest solubility in water [mg/ml] | host (βCD)solubility in water [mg/ml] |
|---|---|---|---|
| Glibenclamide/βCD/ NaOH | 1:3:1 | 5.04 | 34.7 |
| Ibuprofen/βCD/ Triethanolamine | 1:1:1 | 9.0 | 49.5 |
| Indumetacin/βCD/ Triethanolamine | 1:2:2 | 7.2 | 46.0 |
| Furosemide/βCD/ Diethanolamine | 1:2:2 | 7.8 | 53.5 |

From the data reported in the Table 6 the remarkable solubility enhancement of β-cyclodextrin may be observed.

Infact the inherent aqueous solubility of β-cyclodextrin is 18.5 mg/ml.

Moreover we verified whether the increase in solubility of the active ingredient of the complexes of the invention act favourably also on the respective absorption characteristics.

The product resulting from complexation of glibenclamide with βCD and sodium hydroxide was used for these tests. Glibenclamide is a well-known drug, widely used in the treatment of non insulin-dependent diabetes mellitus. It belongs to the sulfonylureas chemical class, which is the most important group of antidiabetics active orally.

The first pharmaceutical formulations of glibenclamide gave rise to variable and incomplete absorption. The active ingredient content of such formulations in conventional tablets was 5 mg for unitary dose.

Subsequent studies allowed to obtain a novel formulation with improved bioavailability, in which the compound is present micronized in an amount of 3.5 mg for unitary dose.

The pharmacokinetic and pharmacodynamic parameters of this novel formulation in tablets are equivalent to those of the conventional formulation.

The inventors compared the absorption rate, the bioavailability and the pharmacodynamic profile of the product obtained by complexation of glibenclamide with βCD and sodium hydroxide (glibenclamide content 3.5 mg) with the best commercial formulation of glibenclamide (Euglucon N 3.5 mg).

EXAMPLE 12

The study was carried out on 6 healthy volunteers which were administered with a single dose of the compounds under test, according to a randomized cross scheme.

Each individual received, in the fasting state, in each of the two test period, separated by a 7 day wash-out interval, a tablet containing the complex of the invention or the reference compound (glibenclamide content of both: 3.5 mg) together with a bolus of 40 g of glucose. 30 minutes later, a second bolus of 50 g of glucose was administered. At different times and up to 12 hours after the administration of the compounds, the plasma concentrations of glibenclamide, insulin and glucose were evaluated.

Table 7 shows the main pharmacokinetic parameters related to glibenclamide determined on the basis of the individual plasma concentrations.

TABLE 7

| Parameters | Reference compound (R) | Test compound (T) | p* | 90% CI T/R** |
|---|---|---|---|---|
| Cmax (ng/mL) | 164 (124; 216) | 289 (224; 371) | 0.01 | 135–231% |
| Tmax (h) | 2.25 (1.0–2.5) | 0.75 (0.75–2.5) | 0.05 | — |
| AUCe (ng. h/mL) | 581 (454; 743) | 641 (531; 776) | N.S. | 100–122% |
| T½abs (h) | 0.38 (017; 0.86) | 0.13 (0.08; 0.23) | 0.05 | 15–78% | b) Cmax = maximum plasma concentration
a) Tmax = time of the maximum concentration
b) AUCe = area under plasma concentration-time curve extrapolated to infinite
b) T½abs = absorption half-life
*= statistical significance of the difference between two formulation means (n.s. = not significant) (P > 0,05)
**= standard confidence interval
a) median value (range)
b) geometric means (±1 SD) (SD = Standard Deviation)

The results show that after the administration of tablets containing the complex of the invention, a remarkably higher absorption rate than that of the reference formulation (about 3 times) is attained, whereas bioavailability, evaluated as the extent of absorption and proved by the AUCθ value, is comparable. The data also evidenced for the complex of the invention a better pharmacodynamic activity profile, since a better control of the glycemic peaks was revealed following glucose intake and higher glycemic levels far from meals.

We claim:

1. A solid multicomponent inclusion complex comprising an acidic drug, a base and a cyclodextrin, said complex obtained by simultaneous salt formation and complexation.

2. The inclusion complex according to claim 1, wherein the base is an inorganic or organic base.

3. The inclusion complex according to claim 1, wherein said cyclodextrin is α-, β- or γ-cyclodextrin.

4. The inclusion complex according to claim 1, wherein said cyclodextrin is a β-cyclodextrin derivative selected from the group consisting of hydroxypropyl-β-cyclodextrin, dimethyl-β-cyclodextrin or RAMEB.

5. The inclusion complex according to claim 1, wherein, in the complex, the molar ratio of cyclodextrin to drug ranges from 0.5 to 10 and the molar ratio of base to drug ranges from 0.1 to 10.

6. The inclusion complex according to claim 1, wherein the cyclodextrin concentration is greater than its inherent aqueous solubility.

7. A process for preparing a multicomponent inclusion complex, comprising the steps of:

a) suspending the desired quantities of an acidic drug, cyclodextrin and base in water or another solvent;

b) homogenizing the suspension obtained in step (a) by stirring and/or sonication thereby obtaining a slightly opalescent solution;

c) filtering the solution of step (b) thereby obtaining a clear solution; and d) drying the solution obtained in step (c).

8. A pharmaceutical composition, comprising:

a therapeutically effective amount of the complex of claim 1 in combination with one or more pharmaceutically acceptable excipients.

9. A process for preparing a multicomponent inclusion complex, comprising the steps of:

a) suspending the desired quantities of an acidic drug, cyclodextrin and base in water or another solvent;

b) homogenizing the suspension obtained in step (a) by stirring and/or sonication thereby obtaining a clear solution; and d) drying the solution obtained in step (b).

* * * * *